(12) United States Patent
Griffin

(10) Patent No.: US 6,252,966 B1
(45) Date of Patent: Jun. 26, 2001

(54) ARTIFICIAL LARYNX

(75) Inventor: Clifford J. Griffin, Temecula, CA (US)

(73) Assignee: Griffin Laboratories, Temecula, CA (US)

( * ) Notice: Subject to any disclaimer, the term of this patent is extended or adjusted under 35 U.S.C. 154(b) by 0 days.

(21) Appl. No.: 09/337,449

(22) Filed: Jun. 21, 1999

(51) Int. Cl.⁷ .................................................. A61F 2/20
(52) U.S. Cl. .................................................. 381/70; 623/9
(58) Field of Search .............................. 381/70, 123, 124; 623/9; 181/126, 127, 128; D24/175

(56) References Cited

U.S. PATENT DOCUMENTS

| D. 358,214 | * | 5/1995 | Breski | D24/175 |
|---|---|---|---|---|
| 3,978,286 | * | 8/1976 | Watson | 381/70 |
| 4,028,492 | * | 6/1977 | Sickel | 381/70 |
| 4,338,488 | * | 7/1982 | Lennox | 381/70 |
| 4,691,360 | * | 9/1987 | Bloomfield, III | 381/70 |
| 4,726,066 | * | 2/1988 | Bloomfield, III | 381/70 |
| 5,812,681 | | 9/1998 | Griffin | 381/70 |

* cited by examiner

Primary Examiner—Xu Mei
(74) Attorney, Agent, or Firm—Loyal McKinley Hanson

(57) ABSTRACT

An artificial larynx includes a case containing a circuitboard subassembly, a battery subassembly, a transducer subassembly, and a switch subassembly that are interconnected to function as means for producing an artificial larynx tone. A radially inwardly extending flange component is bonded with glue or other suitable bonding agent to the cylindrically shaped interior wall of a central case component to provide a screw-less circuitboard mounting stop component for stopping the circuitboard from moving forwardly within the central portion of the case interior in response to battery terminals bearing against a set of rearwardly facing battery connectors on the circuitboard. One embodiment also includes (i) a circuitboard battery cover component and locking ring arrangement, (ii) a silicone, rubber, or other resiliently deformable pad between the switch actuator and the switch for cushioning contact in order to prolong switch life, (iii) a glue-on or machined diaphragm retainer flange that prevents inward diaphragm dislodgement, (iv) two symmetrically disposed grouping of protrusions on the transducer coil form for indicating symmetrically disposed solder joint sites, and (v) first and second stiff wire conductors for electrically connecting the transducer coil contact pads on the circuitboard.

7 Claims, 3 Drawing Sheets

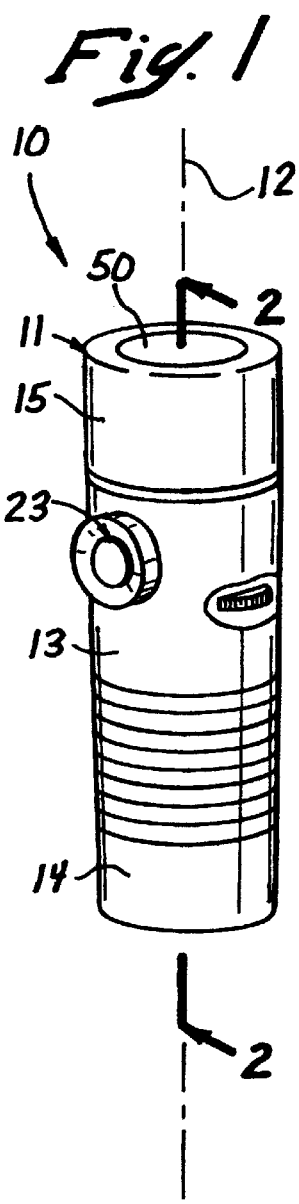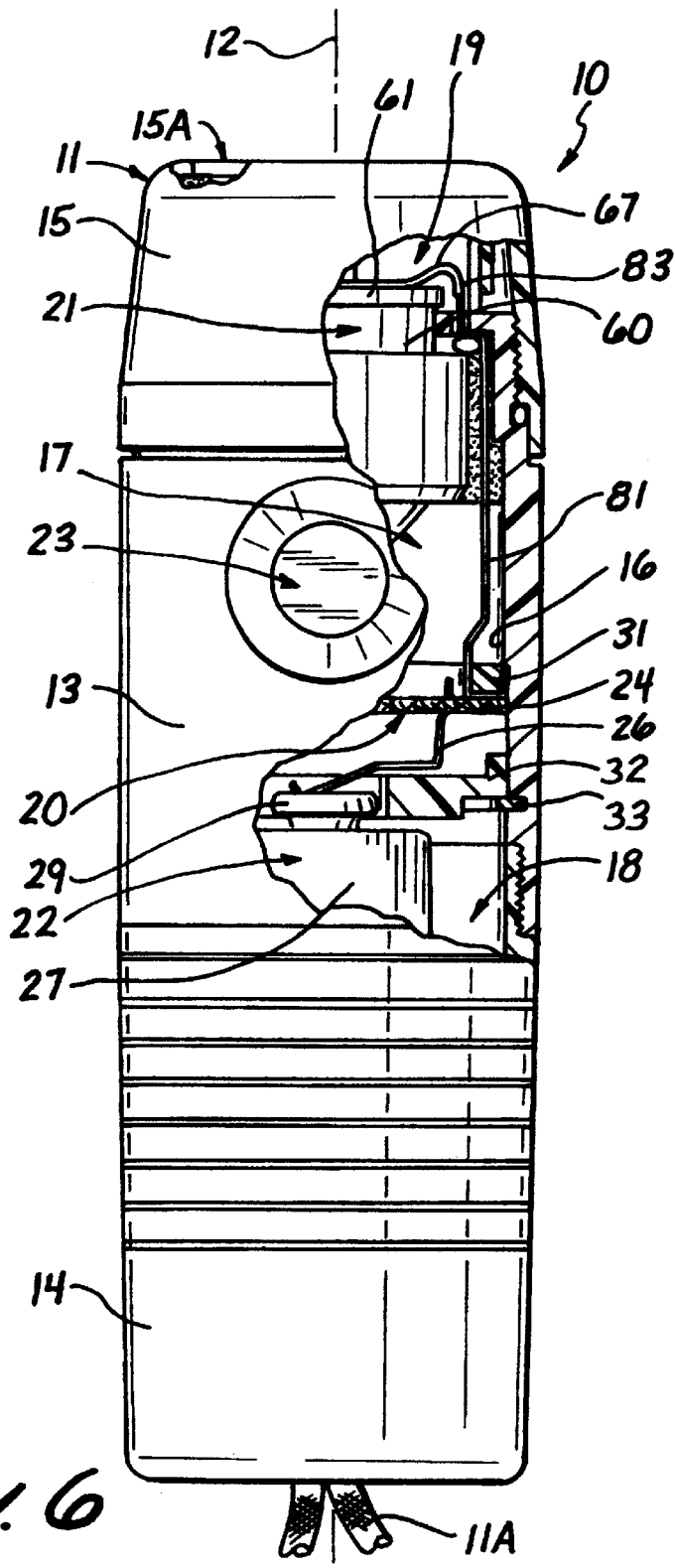

ARTIFICIAL LARYNX

BACKGROUND OF THE INVENTION

1. Technical Field

This invention relates generally to mechanical and electromechanical speech aids commonly referred to as artificial larynxes, and more particularly to an improved electrically powered artificial larynx construction that significantly reduces fabrication time and expense.

2. Description of Related Art

Persons without normal use of their vocal cords or larynx often use an artificial larynx to speak. The artificial larynx produces a tone having a fundamental frequency in the speech range of the average human voice, and the user introduces this artificially generated tone into a resonant speech cavity (i.e., the mouth, nose, or pharynx). To speak, the user modulates the tone by varying the shape of the resonant speech cavity and by making the usual tongue, teeth, and lip constrictions so as to articulate the modulated tone as human speech.

U.S. Pat. No. 5,812,681 issued Aug. 28, 1998 to Clifford J. Griffin describes an ergonomically improved artificial larynx having control components that enable turn-on and frequency control with one pushbutton. Like many existing artificial larynxes, it includes a four to five-inch long cylindrically shaped case that houses a printed circuit board, a battery, an electromechanical transducer for producing vibrations (i.e., the tone), a volume control, and an on-off switch. The user grasps the case, actuates the on-off switch and volume control, and then presses the transducer against the outside of the throat so that vibrations travel through the throat tissues and into the mouth and throat. By varying pressure on the pushbutton switch, the user varies the frequency of the tone to produce a more readily comprehensible voice.

Although effective in many respects, such an artificial larynx shares a problem with other artificial larynxes. That problem is fabrication cost. Assembling all the components in the cylindrical (or other shape) case can be a time consuming and expensive task. Thus, manufacturers need an artificial larynx with details of construction designed to better reduce fabrication costs.

SUMMARY OF THE INVENTION

This invention addresses the problem outlined above by providing an artificial larynx embodying a combination of one or more construction techniques that significantly reduce fabrication cost. A glue-on printed circuitboard support flange reduces component cost and provides a screwless circuitboard subassembly within the artificial larynx case. One embodiment combines that aspect with (i) a circuitboard battery cover component and locking ring arrangement, (ii) a silicone, rubber, or other resiliently deformable pad between the switch actuator and the switch for cushioning contact in order to prolong switch life, (iii) a glue-on or machined diaphragm retainer flange that prevents inward diaphragm dislodgement, (iv) two symmetrically disposed grouping of protrusions on the transducer coil form for indicating symmetrically disposed solder joint sites, and (v) first and second stiff wire conductors for electrically connect the transducer coil contact pads on the circuitboard.

To paraphrase some of the more precise language appearing in the claims, an artificial larynx constructed according to the invention includes a case having a central case component, a rearward case component, and a forward case component that are connected together by threaded engagement of one another to form an artificial larynx case. The artificial larynx case extends along an axis of elongation of the case, the central case component having a cylindrically shaped interior wall that defines a central portion of the case interior, the rearward case component defining a rearward portion of the case interior, and the forward case component defining a forward portion of the case interior. The case component contains a circuitboard subassembly, a transducer subassembly, a battery subassembly, and a switch subassembly that are disposed within the case interior and interconnected to function as means for producing an artificial larynx tone. Those details may be similar in many respects to existing artificial larynxes.

The circuitboard subassembly includes a circuitboard having a forwardly facing side and a rearwardly facing side. The circuitboard subassembly also includes a set of rearwardly facing battery connectors mounted on the circuitboard. The battery subassembly is disposed within the rearward portion of the case interior. It includes a battery having two battery terminals and a spring adapted to bear rearwardly against the rearward case component and forwardly against the battery so that the two battery terminals bear against the set of rearwardly facing battery connectors on the circuitboard.

According to one aspect of the invention, the circuitboard subassembly includes a radially inwardly extending flange component that is bonded with glue or other suitable bonding agent to the cylindrically shaped interior wall of the central case component to function as means for stopping the circuitboard from moving forwardly within the central portion of the case interior in response to the two battery terminals bearing against the set of rearwardly facing battery connectors. That arrangement avoids the molding costs and assembly time of a circuitboard mounting involving screwing tiny screws through the circuitboard into a flange that is molded as part of the central case component. One artificial larynx embodiment combines the screw-less circuitboard mounting with the several other improvements mentioned above to even more significantly reduce fabrication cost and improve switch life. The following illustrative drawings and detailed description make the foregoing and other objects, features, and advantages of the invention more apparent.

BRIEF DESCRIPTION OF THE DRAWINGS

FIG. 1 of the drawings is an isometric view of an artificial larynx constructed according to the invention, showing the front or pushbutton side of the case, together with the right side or volume control side and the distal or forwardly disposed end portion;

FIG. 6 is an enlarged front view taken facing the pushbutton side of the artificial larynx case, with a portion of the case broken away to reveal components within the case.

DESCRIPTION OF A PREFERRED EMBODIMENT

Figure 2:
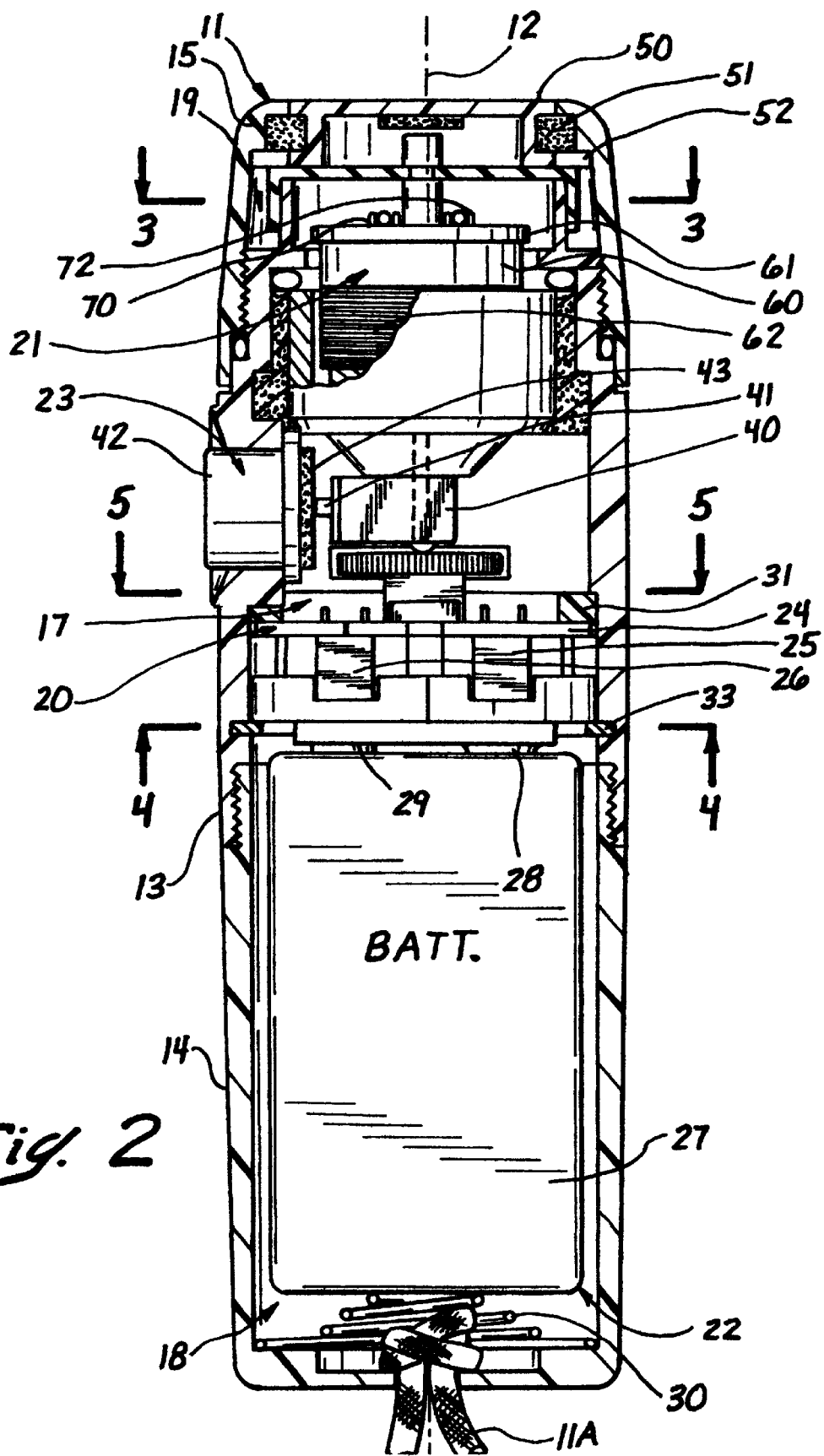
FIG. 2 is an enlarged cross sectional view taken on line 2—2 of FIG. 1.

FIGS. 1–6 of the drawings show various aspects of an artificial larynx 10 constructed according to the invention.

Generally, the artificial larynx 10 includes a case 11 extending along a central axis of elongation 12 (FIG. 1), together with an electrical circuit and various associated components within the case 11. It is similar in many respects to the artificial larynx described in U.S. Pat. No. 5,812,681 issued Sep. 22, 1998 to the same Clifford J. Griffin named as the inventor of the instant invention. That patent is incorporated herein by this reference for the details of construction provided.

The case 11 includes a central case component 13, a proximal or rearward case component 14 (disposed proximally or rearwardly of the central case component 13), and a distal or forward case component 15 (disposed distally or forwardly of the central case component 13). The three case components 13, 14, and 15 are connected together by threaded engagement of one another to form the artificial larynx case 11, with the resulting case 11 having a hollow case interior extending along the axis of elongation 12. The central case component 13 has a cylindrically shaped interior wall 16 (FIG. 6) that defines a central portion 17 (FIGS. 2 and 6) of the case interior. Similarly, the rearward case component 14 defines a rearward portion 18 of the case interior (FIGS. 2 and 6) and the forward case component 15 defines a forward portion 19 of the case interior.

The case 11 may be fabricated from any of various suitable materials (e.g., plastic or metal alloy). It may include a cord 11A (FIGS. 2 and 6) that the user can wear around their neck. As an idea of size, the illustrated case 11 measures about 4.0 to 4.5 inches long and the central portion 13 measures about 1⅝ inches in outside diameter. With those dimensions, the user can easily grip the case 11 in one hand in order to hold it in an operative position against the exterior of their throat. Of course, those dimensions may vary without departing from the inventive concepts disclosed.

The case 11 contains a circuitboard subassembly 20, a transducer subassembly 21, a battery subassembly 22, and a switch subassembly 23 (FIGS. 2 and 6). They are interconnected to function as means for producing an artificial larynx tone. They operate in a manner similar to existing artificial larynxes. But the precise way in which they are constructed and assembled differs for the significant advantages thereby derived.

The circuitboard subassembly 20 is disposed within the central portion 17 of the case interior. It includes a circuitboard 24 and a set of rearwardly facing battery connectors 25 and 26 mounted on the circuitboard 24. The battery subassembly 22 is disposed within the rearward portion 18 of the case interior. It includes a battery 27 having two battery terminals 28 and 29, and a spring 30 adapted to bear rearwardly against the rearward case component 14 and forwardly against the battery 27 so that the two battery terminals 28 and 29 bear forwardly against the set of rearwardly facing battery connectors 25 and 26 on the circuitboard. The battery terminal 28 bears against the battery connector 25 and the battery terminal 29 bears against the battery connector 26.

The circuitboard subassembly 20 includes a radially inwardly extending flange component 31. It is a ring-shaped component that is bonded with glue or other suitable bonding agent to the cylindrically shaped interior wall 16 of the central case component 13. The interior wall 16 measures about 1.25 inches in diameter and the ring shaped flange component 31 has an outside diameter just about 1.25 inches so that the flange component 31 fits against and can be glued to the interior wall 16 during assembly of the artificial larynx 10. The flange component 31 function as means for stopping the circuitboard 24 from moving forwardly within the central portion 17 of the case interior in response to the two battery terminals 28 and 29 bearing against the set of rearwardly facing battery connectors 25 and 26. It does that while avoiding the expense of a flange that is molded as part of the case and while avoiding the fabrication inconvenience and fabrication time involved in screwing the circuitboard to such a molded flange.

Figure 4:
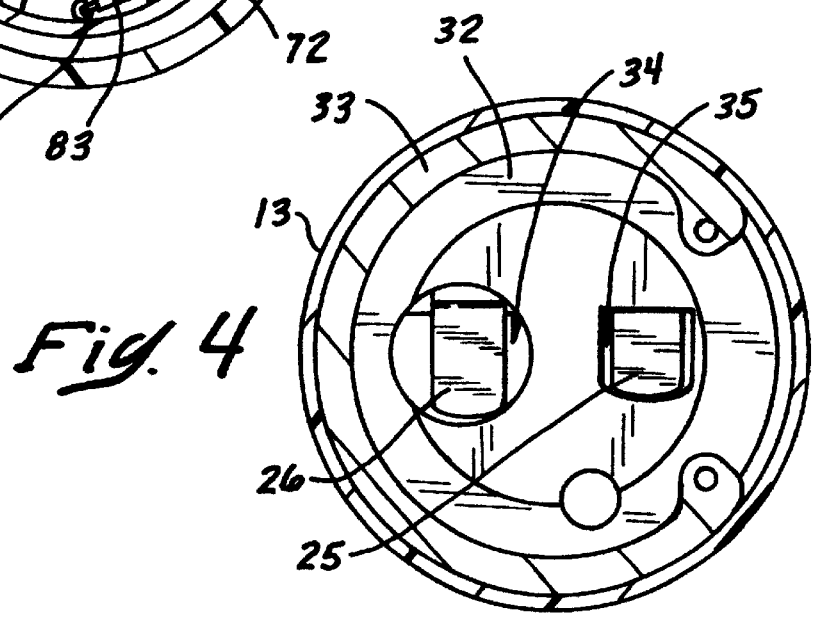
FIG. 4 is a cross sectional view taken on line 4—4 of FIG. 2 that shows details of the circuitboard/battery interface component and retaining ring on the proximal side (the rearwardly disposed battery side) of the circuitboard.
Figure 5:
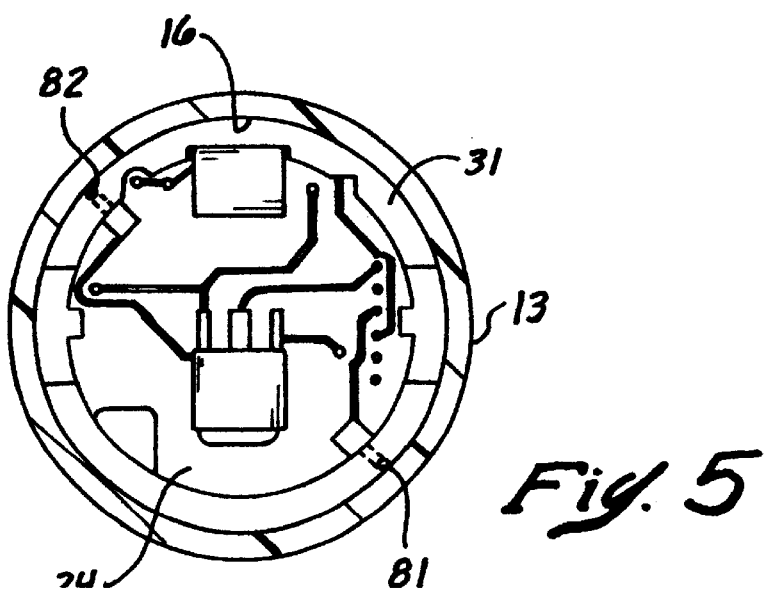
FIG. 5 is a cross sectional view taken on line 5—5 of FIG. 2 that shows details of the circuitboard support component on the distal side of the circuitboard.

A circularly shaped cover component 32 of plastic composition is disposed rearwardly of the circuitboard 24 (FIGS. 2, 4, and 6). It is held against the circuitboard 24 by a retaining ring or locking ring 33. The locking ring 33 is a known type of component. It is a resiliently deformable metal ring (e.g., a spring steel component) that spans less than a full 360-degree arc. It is adapted to be resiliently deformed slightly to reduce its diameter so that it can be placed rearwardly of the circuitboard 24 and then released to recover its shape and hold the circuitboard 24. The locking ring 33 is adapted to engage the central case component 13 that way rearwardly of the cover component 32 in order to stop the circuitboard from moving rearwardly within the central portion 17 of the case interior.

The cover component 32 defines two openings 34 and 35 (FIG. 4) providing access of the two battery terminals 28 and 29 to the set of rearwardly facing battery connectors 25 and 26. The battery 22 is a conventional 9-volt battery having a rectangularly shaped body measuring about 1.0 inches by 0.3125 inches by 1.25 inches. The battery terminal 28 is the positive or male terminal and the battery terminal 29 is the slightly larger negative or female terminal. The opening 34 is sized to accept the battery terminal 28 and the opening 35 is sized to accept the battery terminal 29, thereby assuring proper alignment of the battery with the battery contacts 25 and 26 during assembly.

Now consider the switch subassembly 23. It includes a switch 40 with a switch actuator 41. It also includes a pushbutton 42 and a cushioning pad 43 between the pushbutton 42 and the actuator 41. Depressing the pushbutton 42 causes it to bear against the pad 43 (e.g., a silicone pad) and that causes the pad 43 to bear against the actuator 41 (a plastic component) to thereby operate the switch 40. The inventor of the instant invention has determined that the pad 43 extends the life of the switch 40, and so it is included for that purpose.

Among other things, extended switch life limits the need for repairs and time-consuming disassembly of the artificial larynx 10.

Turning now to the transducer subassembly 21, it includes a circularly shaped diaphragm 50 (FIGS. 1 and 2) with a predetermined outside diameter (e.g., 0.85 inches) and a deformable foam ring 51 (FIG. 2) circumscribing the circularly shaped diaphragm 50. The circularly shaped diaphragm 50 and the foam ring 51 are seated within a circularly shaped opening 15A in the forward case component 15 so that the foam ring 51 allows the diaphragm 50 to vibrate and produce a tone in a known way. In order to designate the opening 15A, a portion of the forward case component 15 and the diaphragm 50 are broken away in FIG. 6.

A retainer ring 52 is glued or otherwise suitably bonded to the forward case component 15 rearwardly of the diaphragm 50 in order to hold the foam ring 52 in place. It takes the place of molded structure in existing devices that defines an annular groove for the foam ring 52 to seat in. Instead of molding an annular groove, the retainer ring 52 is provided and it is sized to have an inside diameter just slightly smaller than the outside diameter of the diaphragm 51 (e.g., 0.837 inches). Besides reducing molding costs and facilitating assembly, the small inside diameter prevents the diaphragm 50 from dislodging rearwardly into the forward case component 15 when the diaphragm 50 is inadvertently bumped or pushed too hard . . . during assembly, in use, or otherwise. In other words, the transducer subassembly 21 includes means for preventing the circularly shaped diaphragm 50 from being unseated by being pushed rearwardly out of the circularly shaped opening 15A, said means including a diaphragm stop component in the form of a ring (i.e., the retainer ring 52) that is bonded to the forward case component 15.

The transducer subassembly 21 also includes a coil form 60 (e.g., a plastic component) that is symmetrical relative to the axis 12 (FIGS. 2, 3, and 6), a circularly shaped end portion 61 of the coil form 60 that faces forwardly (e.g., 0.632 inches in diameter), and a coil of wire 62 on the coil form 60 (FIG. 2). The coil of wire 62 has first and second end portions 64 and 65 (FIG. 3) that are soldered to respective ones of first and second lead wires 66 and 67 to form first and second solder joints 68 and 69. The first and second lead wires 66 and 67 are connected electrically to the circuitboard 24 as subsequently described.

It is important that the first and second solder joints 68 and 69 be located symmetrically relative to the axis 12 to promote proper operation of the transducer subassembly 21. Thus, it is important that the first and second solder joints 68 and 69 be affixed to the circularly shaped end portion 61 of the coil form 60 at symmetrically disposed locations or solder joint sites. For that reason, the circularly shaped end portion 61 is provided with a first grouping 70 of protrusions that function as means for indicating a first solder joint site at which the first solder joint 68 is affixed with glue, epoxy, or other suitable bonding agent 71 (FIG. 3), and a second grouping 72 of protrusions that function as means for indicating a second solder joint site at which the second solder joint 69 is similarly affixed by bonding agent 73.

The first and second groupings 70 and 72 are disposed symmetrically relative to the axis 12 so that the first and second solder joint sites are symmetrically disposed. The illustrated first grouping 70 of protrusions include four protrusions. The leadline for the reference numeral 70 extends to just one of those protrusions. Each illustrated protrusion is a 0.04-inch high 0.20-inch boss that is molded with the rest of the coil form 60 in unitary one-piece construction. The four protrusions indicate the corners of an imaginary 0.10-inch by 0.10-inch square, with the side of each square closest to the axis 12 being about 0.080 inches from the axis 12. The second solder joint site is similarly arranged and the leadline for the reference numeral 72 extends to just one of the four protrusions forming the second solder joint site. Assembly proceeds by soldering the first and second lead wires 66 and 67 to respective ones of the first and second lead wires 66 and 67 to form the first and second solder joints 68 and 69. Then the first and second solder joints 68 and 69 are affixed to the circularly shaped end portion 61 of the coil form 60.

Figure 3:
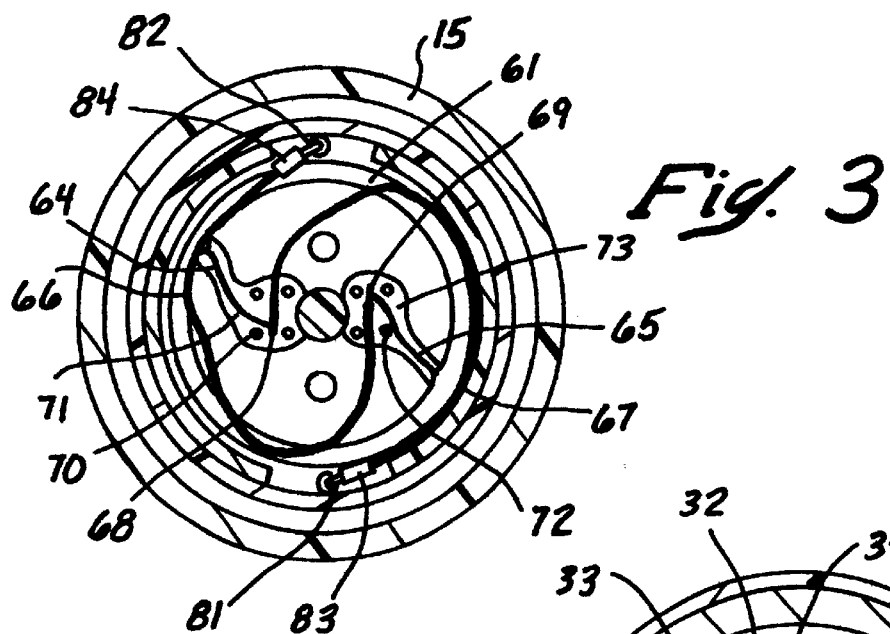
FIG. 3 is a cross sectional view taken on line 3—3 of FIG. 2 that shows details of wire placement on the distal side (the forwardly disposed side) of the transducer coil component.

FIG. 3 also shows forwardly disposed portions of first and second conductors 81 and 82. They are stiff conductors (e.g., copper clad spring steel composition) that electrically connect the first and second lead wires 66 and 67 to the circuitboard 24. They are preferably prefabricated with suitable bends to extend from the first and second lead wires 66 and 67 along the interior of the central case component 13 to the circuitboard 24, as illustrated for the conductor 81 in FIG. 6. The first conductor 81 is connected to the first lead wire 66 by a first a crimp-on connector 83, or other suitable means, and the second conductor 82 is similarly connected to the second lead wire 67 by a second crimp-on connector 84. Rearward portions of the first and second conductors 81 and 82 bear against the circuitboard 24 to effect electrical connection without being soldered or otherwise connected to the circuitboard 24. That arrangement further simplifies assembly and reduces cost.

Thus, the invention provides an artificial larynx embodying a combination of one or more construction techniques that significantly reduce fabrication cost. These include (i) a glue-on printed circuitboard support flange that reduces component cost and provides a screw-less circuitboard subassembly within the artificial larynx case, (ii) a circuitboard battery cover component and locking ring arrangement, (iii) a resiliently deformable pad between the switch actuator and the switch for cushioning contact in order to prolong switch life, (iv) a glue-on or machined diaphragm retainer flange that prevents inward diaphragm dislodgement, (v) two symmetrically disposed grouping of protrusions on the transducer coil form for indicating symmetrically disposed solder joint sites, and (vi) first and second stiff wire conductors for electrically connect the transducer coil contact pads on the circuitboard. Although an exemplary embodiment has been shown and described, one of ordinary skill in the art may make many changes, modifications, and substitutions without necessarily departing from the spirit and scope of the invention.

What is claimed is:

1. An artificial larynx, comprising:
    a case having a central case component, a rearward case component, and a forward case component that are connected together by threaded engagement of one another to form an artificial larynx case extending along an axis of elongation of the case, the central case component having a cylindrically shaped interior wall that defines a central portion of the case interior, the rearward case component defining a rearward portion of the case interior, and the forward case component defining a forward portion of the case interior;
    a circuitboard subassembly, a transducer subassembly, a battery subassembly, and a switch subassembly that are disposed within the case interior and interconnected to function as means for producing an artificial larynx tone;
    the circuitboard subassembly being disposed within the central portion of the case interior, the circuitboard subassembly including a circuitboard having a forwardly facing side and a rearwardly facing side, and the circuitboard subassembly including a set of rearwardly facing battery connectors mounted on the circuitboard;
    the battery subassembly being disposed within the rearward portion of the case interior, the battery subassembly including a battery having two battery terminals and a spring adapted to bear rearwardly against the rearward case component and forwardly against the battery so that the two battery terminals bear against the set of rearwardly facing battery connectors on the circuitboard; and
    the circuitboard subassembly including a radially inwardly extending flange component that is bonded to the cylindrically shaped interior wall of the central case component to function as means for stopping the circuitboard from moving forwardly within the central portion of the case interior in response to the two battery terminals bearing against the set of rearwardly facing battery connectors.

2. An artificial larynx as recited in claim 1, wherein the circuitboard subassembly includes:
   a cover component disposed over the rearwardly facing side of the circuitboard, the cover component defining two openings providing access of the two battery terminals to the set of rearwardly facing battery connectors; and
   a locking ring component adapted to engage the central case component rearwardly of the cover component in order to stop the circuitboard from moving rearwardly within the central portion of the case interior.

3. An artificial larynx as recited in claim 1, wherein the switch subassembly includes:
   a pushbutton switch disposed within the central case component, the pushbutton switch including an actuator;
   means for enabling a user to depress the actuator, including a pushbutton extending through the central case component toward the actuator; and
   cushioning means for cushioning contact of the actuator by the pushbutton in order to prolong the life of the pushbutton switch, including a pad of resiliently deformable material disposed between the pushbutton and the actuator.

4. An artificial larynx as recited in claim 1, wherein the transducer subassembly includes:
   a circularly shaped diaphragm with a predetermined outside diameter and a foam ring circumscribing the circularly shaped diaphragm, with the circularly shaped diaphragm and foam ring being seated within the circularly shaped opening in the forward case component; and
   means for preventing the circularly shaped diaphragm from being unseated by being pushed rearwardly out of the circularly shaped opening, said means including a diaphragm stop component in the form of a ring on the forward case component just rearwardly of the diaphragm, said ring having an inner diameter slightly smaller than an outside diameter of the diaphragm.

5. An artificial larynx as recited in claim 1, wherein the transducer subassembly includes:
   a coil form that is symmetrical relative to the axis of elongation of the case, which coil form includes an circularly shaped end portion that faces forwardly;
   a coil of wire on the coil form, the coil of wire having first and second end portions; and
   first and second lead wires that are soldered to respective ones of the first and second end portions of the coil of wire to form first and second solder joints, which first and second solder joints are affixed to the circularly shaped end portion of the coil form;
   the circularly shaped end portion of the coil form including a first grouping of protrusions that function as means for indicating a first solder joint site at which the first solder joint is affixed and a second grouping of protrusions that function as means for indicating a second solder joint site at which the second solder joint is affixed, which first and second grouping of protrusions are disposed symmetrically relative to the axis of elongation of the case.

6. An artificial larynx as recited in claim 1, wherein:
   the transducer subassembly includes a coil of wire having a first end portion that is connected to a first lead wire and a second end portion that is connected to a second lead wire; and
   the artificial larynx includes first and second stiff wire conductors extending forwardly along the interior of the case from the circuitboard to the first and second lead wires;
   the first and second stiff wire conductors bearing against the circuitboard to thereby effect electrical contact with the circuitboard without being attached to the circuitboard; and
   the first and second stiff wire conductors being physically connected to the first and second lead wires to thereby electrically connect the circuitboard to first and second lead wires.

7. An artificial larynx, comprising:
   a case having a central case component, a rearward case component, and a forward case component that are connected together by threaded engagement of one another to form an artificial larynx case extending along an axis of elongation of the case, the central case component having a cylindrically shaped interior wall that defines a central portion of the case interior, the rearward case component defining a rearward portion of the case interior, and the forward case component defining a forward portion of the case interior;
   a circuitboard subassembly, a transducer subassembly, a battery subassembly, and a switch subassembly that are disposed within the case interior and interconnected to function as means for producing an artificial larynx tone;
   the circuitboard subassembly being disposed within the central portion of the case interior, the circuitboard subassembly including a circuitboard having a forwardly facing side and a rearwardly facing side, and the circuitboard subassembly including a set of rearwardly facing battery connectors mounted on the circuitboard;
   the circuitboard subassembly including a radially inwardly extending flange component that is bonded to the cylindrically shaped interior wall of the central case component to function as means for stopping the circuitboard from moving forwardly within the central portion of the case interior in response to the two battery terminals bearing against the set of rearwardly facing battery connectors;
   the circuitboard subassembly including a cover component disposed over the rearwardly facing side of the circuitboard, the cover component defining two openings providing access of the two battery terminals to the set of rearwardly facing battery connectors, and the circuitboard subassembly including a locking ring component adapted to engage the central case component rearwardly of the cover component in order to stop the circuitboard from moving rearwardly within the central portion of the case interior;
   the battery subassembly being disposed within the rearward portion of the case interior, the battery subassembly including a battery having two battery terminals and a spring adapted to bear rearwardly against the rearward case component and forwardly against the battery so that the two battery terminals bear against the set of rearwardly facing battery connectors on the circuitboard;
   the switch subassembly including a pushbutton switch disposed within the central case component, the pushbutton switch including an actuator, means for enabling a user to depress the actuator, including a pushbutton extending through the central case component toward the actuator, and cushioning means for cushioning contact of the actuator by the pushbutton in order to prolong the life of the pushbutton switch, including a pad of resiliently deformable material disposed between the pushbutton and the actuator; and the transducer subassembly including a coil form that is symmetrical relative to the axis of elongation of the case, which coil form includes an circularly shaped end portion that faces forwardly, a coil of wire on the coil form, the coil of wire having first and second end portions, and first and second lead wires that are soldered to respective ones of the first and second end portions of the coil of wire to form first and second solder joints, which first and second solder joints are affixed to the circularly shaped end portion of the coil form, the circularly shaped end portion of the coil form including a first grouping of protrusions that function as means for indicating a first solder joint site at which the first solder joint is affixed and a second grouping of protrusions that function as means for indicating a second solder joint site at which the second solder joint is affixed, which first and second grouping of protrusions are disposed symmetrically relative to the axis of elongation of the case; and the artificial larynx including first and second stiff wire conductors extending forwardly along the interior of the case from the circuitboard to the first and second lead wires, the first and second stiff wire conductors bearing against the circuitboard to thereby effect electrical contact with the circuitboard without being attached to the circuitboard, and the first and second stiff wire conductors being physically connected to the first and second lead wires to thereby electrically connect the circuitboard to first and second lead wires.

* * * * *